United States Patent
Bolton et al.

(10) Patent No.: US 7,476,259 B2
(45) Date of Patent: *Jan. 13, 2009

(54) HAIR COLOURING COMPOSITIONS

(75) Inventors: Philip David Bolton, Teddington (GB); Jennifer Mary Marsh, Henley on Thames (GB)

(73) Assignee: The Procter & Gamble Company, Cincinnati, OH (US)

( * ) Notice: Subject to any disclaimer, the term of this patent is extended or adjusted under 35 U.S.C. 154(b) by 272 days.

This patent is subject to a terminal disclaimer.

(21) Appl. No.: 11/293,596

(22) Filed: Dec. 2, 2005

(65) Prior Publication Data

US 2006/0117496 A1 Jun. 8, 2006

(51) Int. Cl.
*A61Q 5/10* (2006.01)

(52) U.S. Cl. .................. 8/405; 8/426; 8/435; 8/619; 8/620; 8/107; 8/111

(58) Field of Classification Search .............. 8/405, 8/426, 435, 619, 620, 107, 111
See application file for complete search history.

(56) References Cited

U.S. PATENT DOCUMENTS

| | | | |
|---|---|---|---|
| 5,131,912 A | 7/1992 | Ehara | |
| 6,540,791 B1 * | 4/2003 | Dias | 8/111 |
| 7,044,986 B2 | 5/2006 | Ogawa | |
| 2004/0010865 A1 | 1/2004 | Ogawa | |
| 2004/0019980 A1 | 2/2004 | Au | |
| 2004/0078904 A1 | 4/2004 | Lim | |
| 2004/0083557 A1 | 5/2004 | Au | |
| 2004/0098814 A1 | 5/2004 | Au | |
| 2004/0098816 A1 | 5/2004 | Au | |
| 2005/0102770 A1 | 5/2005 | Kiyomine | |
| 2005/0172419 A1 | 8/2005 | Abe | |

FOREIGN PATENT DOCUMENTS

| | | |
|---|---|---|
| JP | 2001206825 A2 | 7/2001 |
| WO | WO-01/28508 | 4/2001 |
| WO | WO-01/76545 A | 10/2001 |

* cited by examiner

*Primary Examiner*—Eisa B Elhilo
(74) *Attorney, Agent, or Firm*—Melissa Krasovec; Marianne Dressman; Tara Rosnell

(57) ABSTRACT

The present invention relates to an oxidative hair colouring and bleaching composition comprising an oxidizing agent, a source of carbonate ions, an alkalising agent, and preformed dyes, utilised at pH 9.5 and below which improved colour delivery, intensity and vibrancy, which are compatible with current dyes and dye precursor systems. Moreover, the compositions of the present invention also exhibit low odour and deliver a high level of lift and lightening equal to the currently utilised ammonia/peroxide systems, whilst reducing the concentration of peroxide and reducing the hair fibre damage.

10 Claims, No Drawings

HAIR COLOURING COMPOSITIONS

FIELD OF THE INVENTION

The present invention relates to compositions for the bleaching and colouration of keratinous fibres.

BACKGROUND OF THE INVENTION

The permanent alteration of the colour of keratinous fibres, in particular human hair, by the application of hair dyes is well known. In order to provide the consumer with the hair colour and the intensity of colour desired, a very complex chemical process is utilized. Permanent hair dyeing formulations typically comprise oxidative hair dye precursors, which can diffuse into the hair through the cuticle and into the cortex, where they can then react with each other and suitable oxidising agents to form the end dye molecules. Due to the larger size of these resultant molecules they are unable to readily diffuse out of the hair during subsequent washing with water and/or detergents; hence delivering the consumer-desired permanency of colour. This reaction typically takes place in an aggressive environment at approximately pH 10 in the presence of both an alkalizing agent and an oxidizing agent. In addition, preformed dyes may be used either instead of the oxidative hair dye precursors as a method to deliver colour or in combination with oxidative hair dye precursors. These preformed dyes are often intense and chromatic colours and can give the consumer the vibrant shades she desires. Moreover, the consumer repeats the hair dyeing process regularly in order to maintain the desired hair colour and shade and the intensity of colour and to ensure continual, even coverage of the hair including coverage of new hair growth.

The manufacturer of such products is also required to work within a large number of constraints. Since these products are being placed in direct contact with the consumers' skin, the potential exists for accidental contact with the eye or for ingestion (for example), which can occur during the dyeing process. Therefore, the formulations must meet rigorous safety requirements and not induce any allergic reactions. In addition, to meeting these requirements, the products must also be optically and olfactory pleasing to the consumer. In particular, the products need to meet certain physical parameters in order to ensure that the product can be easily applied to the hair by the consumer to provide the desired effect, without unintentional staining of the consumers' clothes, skin, particularly along the hair line, or other objects.

The manufacturer is also required to provide the hair colouring consumer with a large range of different resulting colours. Some consumers may just wish to enhance the natural colour of the hair, whilst others may wish to cover grey or completely alter the hair colour to a different natural appearing hair colour or a 'synthetic' appearing hair colour. Consequently, the manufacturer may provide over twenty different formulations, of varying colours and shades, to address the range of consumer specific needs. These formulations have to be individually formulated and are typically complex formulae containing a mixture of different dye compounds including oxidative and preformed dyes. As a result the manufacture of such product ranges can be costly and complex.

However, despite the fact that commercial hair dyeing products have been available for many years, the products still exhibit a number of consumer-related deficiencies. Typically permanent hair dye products will contain an alkali, typically a source of ammonia. This serves the purpose of swelling the hair, allowing the entry of the dye precursor molecules into the hair and also improves the lightening effect of the oxidising agent, which is typically hydrogen peroxide. However, ammonia is also volatile and its associated odour is extremely unpleasant to the consumers' of such products, particularly as these hair dye products are used in close proximity to the nasal region. Hence, it would be highly desirable to provide an oxidative hair colouring and/or bleaching composition which delivers the consumer required lightening level and colour, but which has reduced or eliminated the detectable ammonia odour.

In fact, another deficiency area in current hair colouring products is the provision of hair colouring products which deliver the required hair colour, especially the required lightening effect and grey hair coverage. The amount of grey hair to be coloured varies considerably from consumer to consumer. The resultant overall appearance of the coloured hair demanded by the consumer should be nearly identical for the naturally pigmented hair, the grey hair on head and new root growth so as to provide even colour deposition from root to tip. Furthermore it is also important that the initial uniform and even colour coverage is maintained during the post dyeing washing and drying cycle.

Delivering the required level of lightening is particularly important in order to provide the full range of colour shades demanded by the consumer, especially for blonde shades requiring yellow and golden tones and grey hair coverage. Such products pose particular difficulties to the manufacturer, as they usually require the use of high levels of oxidising agent and ammonia in order to deliver the required lightening effect. However, in addition to the problems associated with the presence of high levels of ammonia in these products, as discussed herein above, they also affect the condition of the hair and may in some cases induce mild skin irritation on the scalp. In particular, the hydrophilicity of the hair surface is increased during the colouring process, which alters the sensory perception of the hair and its overall manageability during and immediately after colouring, and during the subsequent wash and styling cycles until the next colourant application. Hence, it would also be highly desirable to provide an oxidative hair colouring and/or bleaching composition which delivers the required lightening and/or colour without unnecessary hair damage.

There is also a particular need to provide improved range of dyes which provide colour intensity, vibrancy and strength; typically associated with preformed dyes. However, the use of preformed dyes alone does suffer from restricted application dependant upon the consumers hair colour; for example, red shades are difficult to observe on hair which is dark brown. Consequently a lightening step is required. However preformed dyes are not sufficiently stable in typical oxidant systems, particularly with the persulphate/peroxide bleaches which are used to provide lightening highlights and blondes shades. As a consequence such dyes, if utilised, have to be delivered after the application of the bleaching step thus lengthening and complicating the process for the consumer. Moreover, all of the associated problems of the typical oxidant system are also introduced, such as malodour and fibre damage.

Another critical performance area for the consumer is the time that is required to fully develop the required colour. In particular, the application of hair dye products is still a relatively time consuming process and it may take the consumer over an hour to mix, apply, wait for the final colour to develop and remove the product; before drying and restyling. The majority of current colourant products take a minimum of at least 25 minutes for the final colour to fully develop such that the consumer has to sit with the product applied to the hair for this period of time. Preformed dye systems which deliver the dye rapidly to the hair are however also time consuming if a pre-lightneing step is required. Since for most consumers the hair dyeing process is a regular part of their beauty routine it would be highly desirable if the time required to dye the hair could be reduced whilst still meeting all of the other requirements of ease of application, low odour, and especially, of course, the delivery of the required hair colour, particularly for consumers requiring significant changes and/or levels of lift in the resultant colour.

There are a large number of dyes available which are used in hair colouring products. However, consumer demand for the delivery of specific colours is such that there is still a need to improve and increase the colours provided by hair colourant manufacturers. The development of new dyes however is extremely costly and time consuming and thus the number of new dyes available does not increase significantly over time.

Hence, it would be further desirable to provide the consumer with a hair colourant, providing improved lift and lightening, improved colour delivery, uptake and durability and which provide improved colour and colour variations based upon currently available dyes.

It has now been surprisingly found that hair colouring and/or bleaching systems comprising an oxidizing agent, a source of carbonate ions, an alkalising agent, and preformed dyes, as defined herein below, utilised at pH 9.5 and below, provide hair colouring and bleaching compositions which provide improved uniform root to tip colour delivery and deposition, improved intensity with the required lift and lightening, especially for blonde shades, and excellent grey coverage. Moreover, the compositions of the present invention also surprisingly exhibit low odour and deliver a high level of lift and lightening equal to the currently utilised ammonia/peroxide systems, whilst reducing the concentration of peroxide and reducing the hair fibre damage. The compositions further require less time for application and also deliver excellent wash fastness A number of attempts have been described in the literature to address at least some of the above identified improvement areas. For example, the use of carbonate has been described in the following hair colouring art. However none of these references disclose the claimed features of the present invention.

EP 435 012 describes hair-dyeing compositions, which require a short dyeing time, create little damage to hair, and no irritating odour after dyeing, comprising a carbonate source, a non odour generating alkali hydrogen peroxide and a buffer solution. Similarly EP 1 106 166 describes hair dye compositions comprising ammonia, carbonate (other than ammonia salt), transition metal salt and chelating agent which do not give off an irritating odour, have low skin irritation and can change the hair colour into a lighter tone in a short time. WO01/28508 describes hair colouring formulations comprising oxidising agents and ammonia carbonate or carbamate which deliver improved bleaching and colouring with reduced odour and hair damage without the need for buffering agents, pH modifiers or hair swelling agents. JP01206825 describes a low pungent hair colouring composition comprising ammonia, ammonium salt and carbonate. US2004/0083557 describes hair colouring compositions comprising an oxidative hair dye precursor, a metal cyanate, an alkalizing agent and an oxidizing agent and preferably a metal bicarbonate salt in order to provide good colour lift and low odour. WO04/014328 describes one step hair colouring compositions comprising peroxide oxidizing agents, specific oxidizing agents and at least one water soluble carbonate releasing salts which more effectively deliver colour wherein the composition is applied for a period of from 2 to 60 minutes. US2004/0098814 describes a method of permanently colouring hair whereby the hair is subjected to a number of consecutive short treatments whereby the treatment comprises a dye intermediate in a shampoo or conditioner base, a water soluble carbonate releasing salt and a water soluble ammonium salt. US2004/0098816 also describes a method for the gradual permanent colouring of hair which includes subjecting the hair to a number of treatments having a set time interval between them, wherein the treatment compositions comprise ammonium carbonate in combination with a chelant.

SUMMARY OF THE INVENTION

The present invention relates to a hair colouring or bleaching composition comprising i) at least one source of peroxymonocarbonate ions, ii) at least one source of alkalising agent, preferably ammonium ions iii) at least one preformed dye, wherein said composition has a pH of up to and including pH 9.5

A further aspect the present invention relates to a method of oxidative colouring or oxdaitive bleaching of hair comprising the steps of applying a composition according to the present invention, leaving said composition on the hair for from 2 to 60 minutes and subsequently rinsing said composition from the hair.

Another aspect of the present invention relates to a method of sequential oxidative hair colouring or hair bleaching comprising the steps of at least two sequential oxidative hair colour or hair bleaching treatments wherein the time period between each treatment is from 1 day to 60 days, and wherein each treatment comprises the steps of providing a composition of the present invention and then applying said composition to the hair and retaining said composition on the hair for a time period of less than 20 minutes and subsequently rinsing said composition from the hair.

A further aspect of the present invention relates to a hair colouring or bleaching kit comprising an individually packaged oxidizing component comprising at least one source of hydrogen peroxide and an individually packaged colouring component comprising at least one source of carbonate ions, carbamate ions and or hydrocarbonate ions, and mixtures thereof, at least one alkalising agent, and at least one preformed dye.

DETAILED DESCRIPTION OF THE INVENTION

While the specification concludes with claims, which particularly point out and distinctly claim the invention, it is believed the present invention will be better understood from the following description.

As used herein the term "hair" to be treated may be "living" i.e. on a living body or may be "non-living" i.e. in a wig, hairpiece or other aggregation of non-living keratinous fibers. Mammalian, preferably human hair is preferred. However wool, fur and other keratin containing fibers are suitable substrates for the compositions according to the present invention.

All percentages are by weight of the total composition unless specifically stated otherwise. When more than one composition is used during a treatment, the total weight to be considered is the total weight of all the compositions applied on the hair simultaneously (i.e. the weight found "on head") unless otherwise specified. All ratios are weight ratios unless specifically stated otherwise.

Currently marketed hair permanent colourant products typically utilize a combination of an alkaliser system, dye precursors and an oxidant to deliver the desired hair colour to the consumer. The alkaliser is typically ammonia or an alkanolamine, such as monoethanolamine and the oxidant is typically hydrogen peroxide or a solid form of hydrogen peroxide. The final hair colour which is delivered to the consumer is a combination of the result of the underlying bleaching of the melanin pigment in the hair fibre and the delivery of the coloured dye chromophore moieties which are either preformed, that is direct dyes, or are formed by oxidatization of the dye precursors within the hair fibre.

The optimal pH for such systems is typically about pH 10.0. This high pH is necessary in order to produce a sufficient concentration of the perhydroxy anion (HOO—) to give the desired bleaching of the melanin. It has been found that below pH 9.5 the concentration of this species is less than 0.01% of the added hydrogen peroxide concentration (pKa=11.6) and the amount of melanin bleaching drops dramatically and is hence insufficient to give the desired final colour.

However, as discussed herein above, compositions having a high pH cause many of the disadvantages noted by consumers for these colourant systems. In particular, the level of the volatile ammonia increases at high pH (above pH 9.5) giving increased unpleasant odour. Furthermore, reactive species including the perhydroxy anion reacts with the hair fibre resulting in significant fibre damage. One consequence of this reactivity is that the hydrophilicity of the hair fibres is significantly increased and this causes an increase in the force required to comb the hair compared with hair that has not been coloured. Moreover the higher forces that are exerted during combing and styling result in increased fibre damage to the hair fibres.

It has now been surprisingly found that hair colouring and bleaching compositions comprising the combination of at least one source of peroxymonocarbonate ions, preferably formed insitu from a source of hydrogen peroxide and a carbonate ion source, and at least one source of alkalizing agent and preformed dyes defined hereinafter, at a pH of 9.5 and below can deliver improvements of the desired hair colour results such as improved vibrant colours, improved colour delivery, even colour deposition and wash fastness, whilst reducing the odour and the damage to the hair fibres and requiring less time than currently available products.

Whilst not wishing to be bound by theory, it is believed that in the present invention the key species responsible for the bleaching of the melanin, namely the peroxymonocarbonate ion (—OC(O)OOH), decomposes at pH values above 9.5 to form oxygen and the hydrogen carbonate ion. At pH values below 7.5 the hydrogen carbonate ion decomposes to form carbon dioxide and water. At pH values of 9.0 the bleaching of the melanin and the final colour observed is at an optimal level. Thus, surprisingly, the present invention allows for the delivery of improved lift, that is hair lightening which is a highly desirable consumer need. Furthermore, compositions having a pH lower than 9.5 have the benefit that the unpleasant ammonia odour is significantly reduced which allows for the formation of a hair colouring product that delivers the desired lightening and colour with a pleasant cosmetic-like odour. In addition, the peroxymonocarbonate ions at the lower pH of 9.0 causes less fibre damage than current colouring systems. In particular this gives better hair fibre appearance and thus improved hair shine and colour appearance. Furthermore due to the reduced fibre damage of this system the amount of poor root to tip uptake especially where the tips are heavily damaged either physically (lost cuticle, etc.) or chemically, is significantly reduced resulting in much more even colour deposition. Moreover the wash fastness of the delivered colour is also improved due to the reduced fibre damage of the carbonate system.

Whilst not being bound by theory it is believed the claimed compositions deliver different colours due to its use in the compatible carbonate system verses the incompatible ammonium hydroxide/peroxide systems which must be used independently of the preformed dyes. It is also believed that the carbonate system allows for faster lightening of the hair which in combination with the rapidly delivered preformed dyes, which do not require any development time, results in a composition which more rapidly delivers the desired final colour to the consumer's hair. This means that the application time of the compositions can be significantly reduced.

Oxidizing Agent

The compositions according to the present invention thus comprise a source of peroxymonocarbonate ions. These ions are typically formed insitu from the reaction between a source of hydrogen peroxide and carbonate ion. Consequently, the compositions according to the present invention comprise, or are used in combination with a composition that comprises at least one source of an oxidizing agent. Preferred oxidizing agents for use herein are water-soluble peroxygen oxidizing agents. "Water-soluble" as defined herein means that in standard condition at least 0.1 g, preferably 1 g, more preferably 10 g of said oxidizing agent can be dissolved in 1 liter of deionized water. The oxidizing agents are valuable for the initial solubilisation and decolorisation of the melanin (bleaching) and accelerate the oxidation of the oxidative dye precursors (oxidative dyeing) in the hair shaft.

Any oxidizing agent known in the art may be utilized in the present invention. Preferred water-soluble oxidizing agents are inorganic peroxygen materials capable of yielding hydrogen peroxide in an aqueous solution. Water-soluble peroxygen oxidizing agents are well known in the art and include hydrogen peroxide, inorganic alkali metal peroxides such as sodium periodate and sodium peroxide and organic peroxides such as urea peroxide, melamine peroxide, and inorganic perhydrate salt bleaching compounds, such as the alkali metal salts of perborates, percarbonates, perphosphates, persilicates, persulphates and the like. These inorganic perhydrate salts may be incorporated as monohydrates, tetrahydrates etc. Alkyl and aryl peroxides, and/or peroxidases may also be used. Mixtures of two or more such oxidizing agents can be used if desired. The oxidizing agents may be provided in aqueous solution or as a powder which is dissolved prior to use. Preferred for use in the compositions according to the present invention are hydrogen peroxide, percarbonate (which may be used to provide a source of both oxidizing agent and carbonate ions), persulphates and combinations thereof.

According to the present invention the compositions comprise from about 0.1% to about 10% by weight, preferably from about 1% to about 7% by weight, and most preferably from about 2% to about 5% by weight of an oxidizing agent.

Carbonate Ion Source

According to the present invention the compositions thus also comprise at least a source of carbonate ions or carbamate ions or hydrocarbonate ions or any mixture thereof. Any source of these ions may be utilized. Suitable sources for use herein include sodium, potassium, guanidine, arginine, lithium, calcium, magnesium, barium, ammonium salts of carbonate, carbamate and hydrocarbonate ions and mixtures thereof such as sodium carbonate, sodium hydrogen carbonate, potassium carbonate, potassium hydrogen carbonate, guanidine carbonate, guanidine hydrogen carbonate, lithium carbonate, calcium carbonate, magnesium carbonate, barium carbonate, ammonium carbonate, ammonium hydrogen carbonate and mixtures thereof. Percarbonate salts may also be utilized to provide both the source of carbonate ions and oxidizing agent. Preferred sources of carbonate ions, carbamate and hydrocarbonate ions are sodium hydrogen carbonate, potassium hydrogen carbonate, ammonium carbamate and mixtures thereof.

The compositions of the present invention may comprise from about 0.1% to about 15%, preferably from about 0.1% to about 10% by weight, more preferably from about 1% to about 8% by weight of the carbonate ion. Preferably, if present, the ammonium ions and carbonate ions are present in the composition at a weight ratio of from 3:1 to 1:10, preferably 2:1 to 1:5. In a particularly preferred embodiment of the present invention the ammonium ions and carbonate ion sources are provided by a single source such as ammonium carbonate, ammonium hydrogen carbonate, ammonium hydrocarbonate or mixtures thereof.

Source of Alkalizing Agent

According to the present invention the composition also comprises at least one source of alkalizing agent, preferably a source of ammonium ions and or ammonia. Any agent known in the art may be used such as alkanolamides for example monoethanolamine, diethanolamine, triethanolamine, monopropanolamine, dipropanolamine, tripropanolamine, 2-amino-2-methyl-1, 3-propanediol, 2-amino-2-methyl-1-propanol, and 2-amino-2-hydroxymethyl-1,3-propanediol and guanidium salts. Particularly, preferred alkalizing agents are those which provide a source of ammonium ions. Any source of ammonium ions is suitable for use herein. Preferred sources include ammonium chloride, ammonium sulphate, ammonium nitrate, ammonium phosphate, ammonium acetate, ammonium carbonate, ammonium hydrogen carbonate, ammonium carbamate, ammonium hydroxide, percarbonate salts, ammonia and mixtures thereof. Particularly preferred are ammonium carbonate, ammonium carbamate, ammonia and mixtures thereof The compositions of the present invention may comprise from about 0.1% to about 10% by weight, preferably from about 0.5% to about 5%, most preferably from about 1% to about 3% of an alkalizing agent, preferably ammonium ions.

pH

The compositions of the present invention have a pH up to and including pH 9.5. Preferably, the compositions of the present invention have a pH of from about 9.5 to about 7.5, more preferably from about 9.5 to about 8.4 and most preferably from about 9.4 to about 8.5 and even more preferably about pH 9.0.

Preferably the compositions of the present invention are prepared such that prior to application to the hair fibres the pH of the composition is no greater than about pH 9.5. However, in another embodiment of the present invention the compositions may be formulated such that the pH is up to 9.5 during the time period of application of the composition to the hair fibres prior to removal therefrom. Preferably, the pH is up to about 9.5 for at least 50% of the time period, preferably at least 70%, most preferably at least 80% of the time period of application of the composition to the hair. More preferably, the pH of the composition is up to about pH 9.5 within 10 minutes, preferably within 5 minutes of application to the hair fibres.

The pH of the compositions can be determined by using either a Mettler Toledo MP220 or a MP225 pH equipment, fitted with a standard laboratory pH electrode. The equipment is calibrated before each use using standard calibration buffers and using the standard calibration procedure.

It is known that for good lightening and good colour formation that the final formulation should have a good buffering capacity or reserve alkalinity (the ability of the system to resist the pH shift that would otherwise be caused by addition of acid). The reserve alkalinity is measured using a Mettler DL70 auto-titrator with 0.1N methanolic hydrochloric acid being added to 0.7 mL of thoroughly mixed colourant product in 50 mL of methanol. The electrode is calibrated and then used to measure the amount of acid required to reach the sharpest end point triggered by a rapid change in pH. Using this method it has been determined that a reserve alkalinity of at least 0.2 ml of 0.1N of ethanolic hydrochloric acid and preferably above 0.4 is required for good lightening and colouring. Suitable buffering systems include ammonia/ammonium acetate mixtures, monoethanolamine tetrasodium pyrophosphate, isopropanolamine, benzoic acid.

Dyes

According to the present invention the compositions comprise at least one preformed dye precursor. These compounds are known in the art and include acid dyes, basic dyes, disperse dyes, and reactive dyes. A representative but not exhaustive list can be found in (i) Colour Index 3rd Ed; Society of Dyers & Colourists: Bradford, West Yorkshire & the American Association of Textile Chemists & Colourists: Research Triangle Park 1971 and (ii) International Cosmetic Ingredient Dictionary and Handbook, 10th ed. (2004). Suitable dyes for use herein include:

For example for acid dyes: Acid Red 27 (C.I. 16185), Acid Red 51 (C.I. 45430), Acid Red 18 (C.I. 16255), Acid Red 92 (C.I. 45410), Acid Red 94 (C.I. 45440), Acid Red 52 (C.I. 45100), Acid Yellow 23 (C.I. 19140), Food Yellow 3 (C.I. 15985), Food Green 3 (C.I. 42053), Food Blue 2 (C.I. 42090), Acid Blue 74 (C.I. 73015), Pigment Red 57-1 (C.I. 15850), Acid Red 33 (C.I. 17200), Acid Red 87 (C.I. 45380), Acid Orange 7 (C.I. 15510), Acid Red 95 (C.I. 45425), Acid Yellow 73 (C.I. 45350), Acid Yellow 3 (C.I. 47005), Acid Green 25 (C.I. 61570), Solvent Green 7 (C.I. 59040), Solvent Violet 13, Acid Green 5 (C.I. 42095), Acid Blue 5 (C.I. 42052), Acid Blue 9 (C.I. 42090), Acid Orange 24 (C.I. 20170), Acid Violet 9 (C.I. 45190), Food Red 6 (C.I. 16155), Acid Red 26 (C.I. 16150), Food Red 1 (C.I. 14700), Acid Red 88 (C.I. 15620), Acid Orange 20 (C.I. 14600), Acid Yellow 40 (C.I. 18950), Acid Yellow 1 (C.I. 10316), Acid Yellow 36 (C.I. 13065), Acid Yellow 11 (C.I. 18820), Acid Green 1 (C.I. 10020), Acid Green 3 (C.I. 42085), Acid Violet 43 (C.I. 60730), Acid Black 1 (C.I. 20470), Acid Black 52 (C.I. 15711), Acid Blue 1 (C.I. 42045), Acid Blue 3 (C.I. 42051), Acid Blue 62 (C.I. 62045), Acid Brown 13 (C.I. 10410), Acid Green 50 (C.I. 44090), Acid Orange 3 (C.I. 10385), Acid Orange 6 (C.I. 14270), Acid Red 14 (C.I. 14720), Acid Red 35 (C.I. 18065), Acid Red 73 (C.I. 27290), Acid Red 184 (C.I. 15685), and Brilliant Black 1 (C.I. 28440).

Examples of the basic dyes include Basic Blue 7 (C.I. 42595), Basic Blue 16 (C.I. 12210), Basic Blue 22 (C.I. 61512), Basic Blue 26 (C.I. 44045), Basic Blue 99 (C.I. 56059), Basic Blue 117, Basic Violet 10 (C.I. 45170), Basic Violet 14 (C.I. 42515), Basic Brown 16 (C.I. 12250), Basic Brown 17 (C.I. 12251), Basic Red 2 (C.I. 50240), Basic Red 12 (C.I. 48070), Basic Red 22 (C.I. 11055), Basic Red 51, Basic Red 76 (C.I. 12245), Basic Red 118 (C.I. 12251:1), Basic Orange 31, Basic Orange 69, Basic Yellow 28 (C.I. 48054), Basic Yellow 57 (C.I. 12719), Basic Yellow 87, and Basic Black 2 (C.I. 11825); basic dyes containing a quaternary nitrogen atom in the side chain of an aromatic ring skeleton, the dyes disclosed in, for example, Japanese Patent Publication (kokoku) No. 58-2204 and Japanese Patent Application Laid-Open (kokai) No. 9-118832; and basic dyes disclosed in, for example, Japanese Kohyo Patent Publication No. 10-502946 and Japanese Patent Application Laid-Open (kokai) Nos. 10-182379 and 11-349457.

Examples of the direct dyes other than acid dyes and basic dyes include 2-amino-3-nitrophenol, 2-amino-4-nitrophenol, 2-amino-5-nitrophenol, 4-amino-3-nitrophenol, 2-amino-6-chloro-4-nitrophenol, 4-hydroxypropylamino-3-nitrophenol, 3-nitro-p-hydroxyethylaminophenol, 2-nitro-p-phenylenediamine, 4-nitro-o-phenylenediamine, 4-nitro-m-phenylenediamine, 6-nitro-o-toluidine, 6-nitro-p-toluidine, hydroxyethyl-2-nitro-p-toluidine, N,N'-bis(2-hydroxyethyl)-2-nitro-p-phenylenediamine, 2-chloro-5-nitro-N-hydroxyethyl-p-phenylenediamine, 2-nitro-5-glycerylmethylaniline, 4-amino-2-nitrophenylamine-2-carboxylic acid, 2-chloro-6-ethylamino-4-nitrophenol, 3-methylamino-4-nitrophenoxyethanol, N-ethyl-3-nitro-PABA, picramic acid, 2-hydroxyethylpicramic acid, 4-nitrophenylaminoethylurea, Solvent Violet 13 (C.I.60725), Solvent Yellow 44 (C.I.56200), Disperse Red 17 (C.I.11210), Disperse Violet 1 (C.I.61100), Disperse Violet 4 (C.I.61105), Disperse Black 9, Disperse Blue 377, Disperse Blue 23, Disperse Blue 3 (C.I.61505), Disperse Blue 7 (C.I.62500), HC Violet No. 1, HC Green No. 1, HC Blue No. 2, HC Blue No. 7, HC Blue No. 8, HC Blue No. 9, HC Blue No. 10, HC Blue No. 12, HC Blue No. 14, HC Orange No. 1, HC Orange No. 2, HC Orange No. 3, HC Red No. 1, HC Red No. 3, HC Red No. 7, HC Red No. 8, HC Red No. 9, HC Red No. 10, HC Red No. 11, HC Red No. 13, HC Red No. 14, HC Red No. 16, HC Violet No. 2, HC Yellow No. 2, HC Yellow No. 4, HC Yellow No. 5, HC Yellow No. 6, HC Yellow No. 7, HC Yellow No. 9, HC Yellow No. 10, HC Yellow No. 11, HC Yellow No. 12, HC Yellow No. 13, HC Yellow No. 14 and HC Yellow No. 15.

Preferred preformed dyes for use herein may be selected from Basic Red 51, Basic Orange 31, Basic Yellow 87, Basic Blue 99, Basic Brown 16, Basic Red 76, Basic Yellow 57, Basic Brown 17, Basic red 118, Basic Orange 69, HC Red 3, HC Blue 2, HC Yellow 2, Disperse Blue 377, Acid Violet 43, Solvent Violet 13, 2-amino-6-chloro-4-nitrophenol and mixtures thereof.

The compositions of the present invention will typically comprise from about 0.01% to 10.0% preferably from about 0.01% to 3.0%, by weight of said preformed dyes.

Additional Components

The compositions of the present invention may further comprise additional ingredients which include, but are not limited to, hair dyeing agents such as oxidative dye precursors, non-oxidative dyes, thickeners, solvents, enzymes, surfactants, conditioning agents, carriers, antioxidants, stabilizers, chelants, perming actives, perfume, reducing agents (thiolactic acid), hair swelling agents and/or polymers. Some of these additional components are detailed hereafter.

Hair Dyes

The hair colouring compositions of the present invention may in addition to the preformed dye comprise additional hair dye materials. Such compositions comprise oxidative hair dye precursors (also known as primary intermediates) that will deliver a variety of hair colors to the hair. These small molecules are activated by the oxidizing agent and react with further molecules to form a larger colored complex in the hair shaft. The precursors can be used alone or in combination with other precursors, and one or more can be used in combination with one or more couplers. Couplers (also known as color modifiers or secondary intermediates) are generally colorless molecules that can form colors in the presence of activated precursors, and are used with other precursors or couplers to generate specific color effects or to stabilize the color.

The choice of precursors and couplers will be determined by the color, shade and intensity of coloration that is desired. The precursors and couplers can be used herein, singly or in combination, to provide dyes having a variety of shades ranging from ash blonde to black.

These compounds are well known in the art, and include aromatic diamines, aminophenols, aromatic diols and their derivatives (a representative but not exhaustive list of oxidation dye precursor can be found in Sagarin, "Cosmetic Science and Technology", "Interscience, Special Edn. Vol. 2 pages 308 to 310). It is to be understood that the precursors detailed below are only by way of example and are not intended to limit the compositions and processes herein. These are:

1,7-Dihydroxynaphthalene (1,7-NAPHTHALENEDIOL), 1,3-Diaminobenzene (m-PHENYLENEDIAMINE), 1-Methyl-2,5-diaminobenzene (TOLUENE-2,5-DIAMINE), 1,4-Diaminobenzene (p-PHENYLENEDIAMINE), 1,3-Dihydroxybenzene (RESORCINOL), 1,3-Dihydroxy-4-chlorobenzene, (4-CHLORORESORCINOL), 1-Hydroxy-2-aminobenzene, (o-AMINOPHENOL), 1-Hydroxy-3-aminobenzene (m-AMINOPHENOL), 1-Hydroxy-4-amino-benzene (p-AMINOPHENOL), 1Hydroxynaphthalene (1-NAPHTHOL), 1,5-Dihydroxynaphthalene (1,5-NAPHTHALENEDIOL), 2,7-dihydroxynaphthalene (2,7-NAPHTHELENEDIOL) 1-Hydroxy-2,4-diaminobenzene (4-DIAMINOPHENOL), 1,4-Dihydroxybenzene (HYDROQUINONE), 1-Hydroxy-4-methylaminobenzene (p-METHYLAMINOPHENOL), 6-Hydroxybenzo-morpholine (HYDROXYBENZOMORPHOLINE), 1-Methyl-2-hydroxy-4-aminobenzene (4-AMINO-2-HYDROXY-TOLUENE), 3,4-Diaminobenzoic acid (3,4-DIAMINOBENZOIC ACID), 1-Methyl-2-hydroxy-4-(2'-hydroxyethyl)aminobenzene (2-METHYL-5-HYDROXY-ETHYLAMINO-PHENOL), 1,2,4-Trihydroxybenzene (1,2,4-TRIHYDROXYBENZENE), 1-Phenol-3-methylpyrazol-5-on (PHENYLMETHYLPYRAZOLONE), 1-(2'-Hydroxyethyloxy)-2,4-diaminobenzene (2,4-DIAMINOPHENOXY-ETHANOL HCL), 1-Hydroxy-3-amino-2,4-dichlorobenzene (3-AMINO-2,4-DICHLORO-PHENOL), 1,3-Dihydroxy-2-methylbenzene (2-METHYLRESORCINOL), 1-Amino-4-bis-(2'-hydroxyethyl)aminobenzene (N,N-BIS(2-HYDROXY-ETHYL)-p-PHENYLENE-DIAMINE), 2,4,5,6-Tetraminopyrimidine (HC Red 16), 1-Hydroxy-3-methyl-4-aminobenzene (4-AMINO-m-CRESOL), 1-Hydroxy-2-amino-5-methylbenzene (6-AMINO-m-CRESOL), 1,3-Bis-(2,4-Diaminophenoxy)propane (1,3-BIS-(2,4-DIAMINO-PHENOXY)-PROPANE),1-(2'-Hydroxyethyl)-2,5-diaminobenzene (HYDROXYETHYL-p-PHENYLENE DIAMINE SULPHATE), 1-Methoxy-2-amino-4-(2'-hydroxyethylamino) benzene, (2-AMINO-4-HYDROXYETHYLAMINOANISOLE) 1-Hydroxy-2-methyl-5-amino-6-chlorobenzene (5-AMINO-6-CHLORO-o-CRESOL), 1-Hydroxy-2-amino-6-methylbenzene (6-AMINO-o-CRESOL), 1-(2'-Hydroxyethyl)-amino-3,4-methylenedioxybenzene (HYDROXYETHYL-3,4-METHYLENEDIOXY-ANILINE HCl), 2,6-Dihydroxy-3,4-dimethylpyridine (2,6-DIHYDROXY-3,4-DIMETHYLPYRIDINE), 3,5-Diamino-2,6-dimethoxypyridine (2,6-DIMETHOXY-3,5-PYRIDINEDIAMINE), 5,6-Dihydroxyindole (,DIHYDROXY-INDOLE), 4-Amino-2-aminomethylphenol (2-AMINOETHYL-p-AMINO-PHENOL HCl), 2,4-Diamino-5-methylphenetol (2,4-DIAMINO-5-ME- THYL-PHENETOLE HCl), 2,4-Diamino-5-(2'-hydroxyethyloxy)toluene (2,4-DIAMINO-5-METHYLPHENOXYETHANOL HCl), 5-Amino-4-chloro-2-methylphenol (5-AMINO-4-CHLORO-o-CRESOL), 4-Amino-1-hydroxy-2-(2'-hydroxyethylaminomethyl) benzene HYDROXYETHYLAMINOMETHYL-p-AMINO PHENOL HCl), 4-Amino-1-hydroxy-2-methoxymethylbenzene (2-METHOXYMETHYL-p-AMINOPHENOL HCl), 1,3-Bis(N(2-Hydroxyethyl)N(4-amino-phenyl)amino)-2-propanol (HYDROXYPROPYL-BIS-(N-HYDROXY-ETHYL-p-PHENYLENEDIAMINE)HCL), 6-Hydorxyindole (6-HYDROXY-INDOLE), 2,3-Indolinedione (ISATIN), 3-Amino-2-methylamino-6-methoxypyridine (HC BLUE NO. 7), 1-Phenyl-3-methyl-5-pyrazolone-2,4-dihydro-5, 2-phenyl-3H-pyrazole-3-one, 2-Amino-3-hydroxypyridine (2-AMINO-3-HYDROXYPYRIDINE), 5-Aminosalicylic acid, 1-Methyl-2,6-bis(2-hydroxy-ethylamino) benzene (2,6-HYDROXYETHYLAMINO-TOLUENE), 4-Hydroxy-2,5,6-triaminopyrimidine (2,5,6-TRIAMINO-4-PYRIMIDINOL SULPHATE), 2,2'-[1,2-Ethanediyl-bis-(oxy-2,1-ethanediyloxy)]-bis-benzene-1,4-diamine (PEG-3,2',2'-DI-p-PHENYLENEDIAMINE), 5,6-Dihydroxyindoline (DIHYDROXYINDOLINE), N,N-Dimethyl-3-ureidoaniline (m-DIMETHYL-AMINO-PHENYLUREA), 2,4-Diamino-5-fluortoluenesulfatehydrate (4-FLUORO-6-METHYL-m-PHENYLENEDIAMINE SULPHATE) and 1-Acetoxy-2-methylnaphthalene (1-HYDROXYYETHYL-4,5-DIAMINOPYRAZOLE SULPHATE). These can be used in the molecular form or in the form of peroxide-compatible salts.

Preferred oxidative precursors may be selected from 2-methyl-benzene-1,4-diamine; benzene-1,4-diamine; N,N-Bis(2-hydroxyethyl)-p-phenylenediamine; 4-amino-phenol; 4-methylamino-phenol; 4-amino-3-methyl-phenol; 1-Hydroxy-2,4-diaminobenzene; 2-amino-phenol; 2-amino-5-methyl-phenol; 2-amino-6-methyl-phenol; 1-methyl-1H-pyrazole-4,5-diamine; 1-Hydroxyethyl-4,5-diaminopyrazole sulphate; 2-(4,5-diamino-1H-pyrazol-1-yl)ethanol;

benzene-1,3-diol; 4-chlorobenzene-1,3-diol; 2-methyl-benzene-1,3-diol; benzene-1,3-diamine; 3-amino-phenol; 5-amino-2-methyl-phenol; 1-Methyl-2-hydroxy-4-(2'-hydroxyethyl)aminobenzene; 4-methyl-2-phenyl-2,4-dihydro-3H-pyrazol-3-one; 2-aminopyridin-3-ol; 1-phenyl-3-methylpyrazol-5-one; 1-Phenyl-3-methyl-5-pyrazolone-2,4-dihydro-5,2-phenyl-3H-pyrazole-3-one; and mixtures thereof.

The hair dye compositions of the present invention will generally comprise from about 0.001% to about 10% of dyes. For example compositions providing low intensity dyeing such as natural blonde to light brown hair shades generally comprise from about 0.001% to about 5%, preferably from about 0.1% to about 2%, more preferably from about 0.2% to about 1% by weight of dyeing composition of precursors and couplers. Darker shades such as browns and black typically comprise from 0.001% to about 10% by weight, preferably from about 0.05% to about 7% by weight, more preferably form about 1% to about 5% of precursors and couplers.

Radical Scavenger

According to the present invention the compositions may comprise of a source of radical scavenger. As used herein the term radical scavenger refers to a species that can react with a carbonate radical to convert the carbonate radical by a series of fast reactions to a less reactive species, i.e. a carbonate radical scavenger. Radical scavengers include compounds according to the general formula:

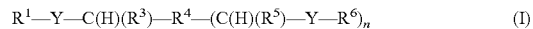

$$R^1-Y-C(H)(R^3)-R^4-(C(H)(R^5)-Y-R^6)_n \qquad (I)$$

wherein Y is $NR^2$, O, or S, preferably $NR^2$, n is 0 to 2, and wherein $R^4$ is monovalent or divalent and is selected from: (a) substituted or unsubstituted, straight or branched, alkyl, mono- or poly-unsaturated alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; the systems of (a), (b) and (c) comprising from 1 to 12 carbon atoms and 0 to 5 heteroatoms selected from O, S, N, P, and Si; and wherein $R^4$ can be connected to $R^3$ or $R^5$ to create a 5, 6 or 7 membered ring; and wherein $R^1$, $R^2$, $R^3$, $R^5$, and $R^6$ are monovalent and are selected independently from: (a), (b) and (c) described herein above, or H.

Preferably, $R^4$ is selected from: (a) substituted or unsubstituted, straight or branched, alkyl, heteroalkyl, aliphatic, heteroaliphatic, or heteroolefinic systems, (b) substituted or unsubstituted, mono- or poly-cyclic aliphatic, aryl, or heterocyclic systems, or (c) substituted or unsubstituted, mono-, poly-, or per-fluoro alkyl systems; more preferably $R^4$ is selected from (a) substituted or unsubstituted, straight or branched, alkyl, heteroalkyl, aliphatic, or heteroaliphatic systems, (b) substituted or unsubstituted, aryl, or heterocyclic systems, or (c) substituted or unsubstituted, mono-, poly-, or per-fluoro alkyl systems; more preferably substituted or unsubstituted, straight or branched, alkyl, or heteroalkyl systems.

Preferably, the $R^4$ systems of (a), (b), and (c), described herein above, comprise from 1 to 8 carbon atoms, preferably from 1 to 6, more preferably from 1 to 4 carbon atoms and from 0 to 3 heteroatoms; preferably from 0 to 2 heteroatoms; most preferably from 0 to 1 heteroatoms. Where the systems contain heteroatoms, preferably they contain 1 heteroatom. Preferred heteroatoms include O, S, and N; more preferred are O, and N; and most preferred is O.

Preferably, $R^1$, $R^2$, $R^3$, $R^5$, and $R^6$ are selected independently from any of the systems defined for $R^4$ above, and H. In alternative embodiments, any of $R^1$, $R^2$, $R^3$, $R^4$, $R^5$, and $R^6$ groups are substituted. Preferably, the substituent(s) is selected from: (a) the group of C-linked monovalent substituents consisting of: (i) substituted or unsubstituted, straight or branched, alkyl, mono- or poly-unsaturated alkyl, heteroalkyl, aliphatic, heteroaliphatic, or heteroolefinic systems, (ii) substituted or unsubstituted, mono- or poly-cyclic aliphatic, aryl, or heterocyclic systems, or (iii) substituted or unsubstituted, mono-, poly-, or per-fluoro alkyl systems; said systems of (i), (ii) and (iii) comprising from 1 to 10 carbon atoms and 0 to 5 heteroatoms selected from O, S, N, P, and Si; (b) the group of S-linked monovalent substituents consisting of $SA^1$, SCN, $SO_2A^1$, $SO_3A^1$, $SSA^1$, $SOA^1$, $SO_2NA^1A^2$, $SNA^1A^2$, and $SONA^1A^2$; (c) the group of O-linked monovalent substituents consisting of $OA^1$, OCN and $ONA^1A^2$; (d) the group of N-linked monovalent substituents consisting of $NA^1A^2$, $(NA^1A^2A^3)^+$, NC, $NA^1OA^2$, $NA^1SA^2$, NCO, NCS, $NO_2$, $N=NA^1$, $N=NOA^1$, $NA^1CN$, $NA^1NA^2A^3$; (e) the group of monovalent substituents consisting of $COOA^1$, $CON_3$, $CONA^1_2$, $CONA^1COA^2$, $C(=NA^1)NA^1A^2$, CHO, CHS, CN, NC, and X; and (f) the group consisting fluoroalkyl monovalent substituents consisting of mono-, poly-, or per-fluoro alkyl systems comprising from 1 to 12 carbon atoms and 0 to 4 heteroatoms.

For the groups (b) to (e), described above, $A^1$, $A^2$, and $A^3$ are monovalent and are independently selected from: (1) H, (2) substituted or unsubstituted, straight or branched, alkyl, mono- or poly-unsaturated alkyl, heteroalkyl, aliphatic, heteroaliphatic, or heteroolefinic systems, (3) substituted or unsubstituted, mono- or poly-cyclic aliphatic, aryl, or heterocyclic systems, or (4) substituted or unsubstituted, mono-, poly-, or per-fluoro alkyl systems; said systems of (2), (3) and (4) comprising from 1 to 10 carbon atoms and 0 to 5 heteroatoms selected from O, S, N, P, and Si; and wherein X is a halogen selected from the group consisting of F, Cl, Br, and I.

Preferably the above defined radical scavengers have a pKa of more than 7 to prevent the protonation of the nitrogen.

Surfactants

The compositions according to the present invention may further comprise at least about 0.01% of a surfactant. Surfactants suitable for use herein generally have a lipophilic chain length of from about 8 to about 30 carbon atoms and can be selected from anionic, nonionic, amphoteric and cationic surfactants and mixtures thereof.

Polymers

The composition of the present invention may optionally further comprise at least about 0.01% of polymer. The polymer can be chosen, for example, from associative polymers, crosslinked acrylic acid homopolymers, crosslinked copolymers of (meth)acrylic acid and of (C1-C6)alkyl acrylate or polysaccharides. The polymer may serve as a thickening agent and also serve as conditioning agents, as described below. The polymer will generally be used at levels of from about 0.01% to about 20.0% by weight of the composition, preferably of from about 0.1% to about 5%.

Conditioning Agent

The compositions of the present invention may comprise or are used in combination with a composition comprising a conditioning agent. Conditioning agents suitable for use herein are selected from silicone materials, amino silicones, fatty alcohols, polymeric resins, polyol carboxylic acid esters, cationic polymers, cationic surfactants, insoluble oils and oil derived materials and mixtures thereof. Additional materials include mineral oils and other oils such as glycerin and sorbitol. Particularly useful conditioning materials are cationic polymers and silicones. Conditioners of the cationic polymer type can be chosen from those comprising units of at least one amine group chosen from primary, secondary, tertiary and quaternary amine groups that may either form part of the main polymer chain, or be borne by a side substituent that is directly attached to the main polymer chain.

Silicones can be selected from polyalkylsilioxane oils, linear polydiemthylsiloxane oils containing trimethylsilyl or hydroxydimethylsiloxane endgroups, polymethylphenylsiloxane polydimethylphenylsiloxane or polydimethyldiphenylsiloxane oils, silicone resins, organofunctional siloxanes having in their general structure one or a number of organofunctional group(s), the same or different, attached directly to the siloxane chain or mixtures thereof. Said organofunctional group(s) are selected from: polyethyleneoxy and/or polypropyleneoxy groups, (per)fluorinated groups, thiol groups, substituted or unsubstituted amino groups, carboxylate groups, hydroxylated groups, alkoxylated groups, quaternium ammonium groups, amphoteric and betaine groups. The silicone can either be used as a neat fluid or in the form of an pre-formed emulsion.

The conditioning agent will generally be used at levels of from about 0.05% to about 20% by weight of the composition, preferably of from about 0.1% to about 15%, more preferably of from about 0.2% to about 10%, even more preferably of from about 0.2% to about 2%.

Chelants

According to the present invention the compositions may comprise chelants. Chelants are well known in the art and refer to a molecule or a mixture of different molecules each capable of forming a chelate with a metal ion. Chelants are well known in the art and a non-exhaustive list thereof can be found in A E Martell & R M Smith, Critical Stability Constants, Vol. 1, Plenum Press, New York & London (1974) and A E Martell & R D Hancock, Metal Complexes in Aqueous Solution, Plenum Press, New York & London (1996) both incorporated herein by reference.

Examples of chelants suitable for use herein include EDDS (ethylenediaminedisuccinic acid), carboxylic acids (in particular aminocarboxylic acids), phosphonic acids (in particular aminophosphonic acids) and polyphosphoric acids (in particular linear polyphosphoric acids), their salts and derivatives.

Chelants may be incorporated into the composition of the present invention as stabilizers and or preservatives. In addition it has also been found that chelants provide hair fibre damage benefits and thus they may be utilized in order to further improve the hair damage profile of the present invention. Levels of chelants in the present invention may be as low as about 0.1%, preferably at least about about 0.25%, more preferably about 0.5% for the most effective chelants such as diamine-N,N'-dipolyacid and monoamine monoamide-N,N'-dipolyacid chelants (for example EDDS). Less effective chelants will be more preferably used at levels of at least about 1%, even more preferably above about 2% by weight of the composition, depending of the efficiency of the chelant. Levels as high as about 10% can be used, but above this level significant formulation issues may arise.

Solvents

Suitable solvents for use in the compositions of the present invention include, but are not limited to, water, butoxydiglycol, propylene glycol, alcohol (denat.), ethoxydiglycol, isopropylalcohol, hexylene glycol, benzyl alcohol and dipropylene glycol.

Finally, the compositions according to the present invention can be provided in any usual form, such as for example an aqueous composition, a powder, a gel or an oil-in-water emulsion. A preferred form for the compositions according to the present invention is thickened solutions comprising a salt-tolerant thickener or oil-in-water emulsions.

It is understood that the examples of methods of use and embodiments described herein are for illustrative purposes only and that various modifications or changes in light thereof will be suggested to one skilled in the art without departing from the scope of the present invention.

Oxidative hair dye compositions are usually sold in kits comprising, in individually packaged components such as separate containers, a dye component (also called "dye cream" for emulsions or "dye liquid" for solutions) comprising the oxidative dye, precursors and alkalizing agent in a suitable carrier and; a hydrogen peroxide component (also called "hydrogen peroxide cream" for emulsions or "hydrogen peroxide liquid" for solutions) comprising the oxidizing agent. According to the present invention the preformed dyes may be comprised within the dye component or alternatively they may be comprised in a separate preformed dye component. The consumer mixes the dye component(s) and hydrogen peroxide component together immediately before use and applies it onto the hair. The exemplified formulations given in the tables hereinafter illustrate these resulting mixtures.

After working the mixture for a few minutes (to insure uniform application to all of the hair), the oxidative dye or bleaching composition is allowed to remain on the hair for an amount sufficient for the dyeing to take place (usually about 2 to 60 minutes preferably from about 30 to 45 minutes). The consumer then rinses his/her hair thoroughly with tap water and allows it to dry. It is observed that the hair has changed from its original color to the desired color.

When present in the oxidative dye compositions and bleaching compositions, the optional conditioning agent can be provided in a third container. In the latter case, all three compositions can be mixed immediately before use and applied together, or the content of the third container can be applied (after an optional rinse step) as a post-treatment immediately after the oxidative dye composition or bleaching composition resulting from the mixture of the other containers.

The present invention may be utilized in a variety of packaging and dispensing devices. These dispensing devices can come in the form of separate devices which may be used independently or in combination with one another. Typically, the hair colouring or bleaching compositions are contained within separate single or multi compartment containers so that the compositions can be stored separately from one another before use. The compositions are then mixed together by a mixing means and then applied to the consumer's hair by an application means.

The most common packaging device which can be used for the present invention involves storing the developer in a container such as a bottle, tube, aerosol, or a sachet and separately storing the dye lotion in an additional compartment within the developer container or in a separate container which may be identical such as a dual sachet or aesrosol systems for example or different such as a bottle and tube system.

The consumer may mix the developer lotion and the dye lotion by any means. This may simply involve the use of a mixing bowl into which the lotions are dispensed and then mixed, preferably using a mixing means such as a tool. Alternatively it may involve the addition of one of the lotions into the container of the other lotion, (typically the dye lotion is added to the developer lotion), followed by manual shaking or mixing with a tool. Another system involves the perforation or displacement of a seal located between the separate compartments of the dye and developer lotion within a single container or sachet followed by manual mixing within the container or in a separate and or additional container.

An example of such devices are the so called 'twist and go' devices. These devices allow the consumer to twist the base of a container holding the dye which enables a communication port to open that exposes the base of the bottle holding the dye and the top of the bottle holding the developer. The two components are mixed and the consumer dispenses the product by squeezing the flexible top portion of the bottle for dispensing.

Alternatively more complex devices may be utilised, whereby the lotions are mixed upon actuation of dispensing. An example of such as a complex system is a dual aerosol system e.g. bag-in-can or piston. The dye and developer are stored separately in two aerosol cans within one device, a propellant being used to pressurize the contents of the can or bag in can or piston and a valve providing the control of dispensation. When the consumer actuates the valve, the dye and developer are dispensed simultaneously out of the cans and are mixed together via a static mixer just before dispensing the product onto the hair. The ratio of the dye and developer can be manipulated by the viscosity of the products, the can pressure, or by altering the flow channel sizes through the valve. Additionally, the product can be foamed and delivered via a mousse form.

Another example of such a complex system utilises a dual piston screw system. The dye and the developer are kept in separate piston cylinder systems within the system and when the consumer actuates a button, two screws are rotated such that the dual pistons inside pressurize the liquid in the cylinders and thus force the products to move through a mixing station and out of the nozzle for dispensing. The ratios of the dye and the developer can be manipulated by the diameter of the cylinder of the package. Additionally, an in line static mixer can be used to aid mixing and such a system can be completely disposable or completely refillable.

Yet another system utilises one or more manually actuated pumps. The product may be premixed in a collapsible sachet. When the consumer actuates the pump, the liquid inside the pump is dispensed. As the manually actuated pump returns to the upright position it forces product from a collapsible sachet. Alternatively, a dual system can be installed whereby two sachets and two pumps are used to deliver the dye and the developer lotions to the hair. Alternatively, a single pump connected to two sachets can deliver the product by incorporating the mixing point within the pump. Another embodiment uses a rigid bottle and a dip tube to connect the product to the pump system. Finally, a delaminating bottle can be used in combination with a manually actuated pump where the inner layer of the bottle separates from the outer layer of the bottle which forces the contents of the bottle to be emptied.

Typically these complex systems offer the advantage of product application independently of the orientation of the product.

The devices described herein above can also be used in combination with a product delivery and or application tool to aid application of the product onto the hair. Again these devices may be of a very simple nature such as a nozzle attached to one of the containers or a separate applicator device such as a comb or brush. Such combs and brushes can be adapted in order to achieve particular effects, whether it be quick and even coverage or root/hairline touch up, or highlights or streaks. Alternatively, the container or one of the containers may be provided with a comb attached to or instead of the dispensing nozzle whereby the product is dispensed through hollow tines and dispensing apertures located in the comb tines. The comb tines may be provided with single or multiple openings along the tines to improve product application and evenness especially root to tip. Product dispensation can be achieved by mechanical pressure applied to the container for example delaminating bottles or any of the mechanisms described hereinabove. The comb may be provided on the container such as to facilitate easy application and may be positioned vertically (so called verticomb) or at an angle to allow the consumer to access all areas. All devices may be designed to have inter-changeability, so that a range of different tools for hair application can be provided to the consumer.

The application devices may also include devices which assist in achieving particular effects such as highlighting such as highlighting combs, brushes and tools, foils and highlighting caps.

Additional device technology can be used to assist in the penetration of the product into the hair. Examples of such technology include heating devices, ultraviolet light devices and ultrasound devices.

Method of Use

According to one method of oxidatively colouring and or bleaching hair according to the present invention, this comprises the steps of applying an oxidising hair colouring composition of the present invention having a pH of up to 9.5 when applied to the hair of the consumer, or have a pH that is up to 9.5 for at least 50% of the time period the composition is applied to the hair. Alternatively, the individual compositions may have varying pH levels such that on mixing or application to the consumer the pH is up to 9.5.

According to the present invention the methods of colouring or bleaching hair also comprise embodiments whereby the composition of the present invention is applied to the hair and preferably the mixture is worked for a few minutes (to insure uniform application to all of the hair). The composition is then allowed to remain on the hair in order for the colour to develop for a time period of less than about 20 minutes, preferably less than about 15 minutes, more preferably from about 5 minutes to about 10 minutes, most preferably for about 10 minutes. The consumer then rinses his/her hair thoroughly with water and allows it to dry and/or styles the hair as usual.

According to a further alternative embodiment of the present invention, the method of colouring and or bleaching the hair is a sequential oxidative hair colouring or hair bleaching method comprising the steps of at least two sequential oxidative hair colour or hair bleaching treatments wherein the time period between each treatment is from 1 to 60 days, preferably from 1 to 40 days, more preferably from 1 to 28 days, even more preferably from 1 to 14 days and most preferably from 1 to 7 days. In such embodiments the time that the composition is retained on head may be less than about 20 minutes and is preferably less than about 10 minutes and most preferably from about 2 minutes to about 5 minutes.

The kits described hereinabove are well known in the art and the composition in each container can be manufactured utilizing any one of the standard approaches, these include a) 'Oil in water' process, b) 'Phase Inversion' process and c) 'One-pot' process.

For example, in a 'One-pot' process, the polymers and chelants would be pre-dissolved in water, the fatty materials added and then the whole composition heated to about 70-80° C. A controlled cooling and optional shearing process to form the final structured product in the case of an emulsion would then follow. Addition of the materials providing a source of peroxymonocarbonate ions, dyes and ammonia, and optionally solvents, and pH trimming complete the making process of the dye cream.

In the case of a liquid solution comprising acrylate polymers, these would be formulated into the hydrogen peroxide component. The glycol solvents and fatty components are formulated into the dye component. A structured product is formed when the dye and hydrogen peroxide components are mixed together prior to use of the composition, resulting from deprotonation of the polymer acrylic acid groups as the pH rises, yielding a polymeric micro-gel. Further details on the manufacture of these two-part aqueous composition for coloring hair, which forms a gel on mixing of the two parts can be found in U.S. Pat. No. 5,376,146, Casperson et al. and U.S. Pat. No. 5,393,305, Cohen et al.

The composition of the present invention can also be formulated as 2-part aqueous compositions comprising polyetherpolyurethane as thickening agent (such as Aculyn® 46) as described in U.S. Pat. No. 6,156,076, Casperson et al. and U.S. Pat. No. 6,106,578, Jones.

EXAMPLES

The following examples illustrate oxidative colouring compositions according to the present invention and methods of manufacture thereof. It is understood that the examples and embodiments described herein are for illustrative purposes only and that various modifications or changes in light thereof will be suggested to one skilled in the art without departing from the scope of the present invention.

Examples of Emulsion Formulations 1-10

| Ingredient | Formulation | | | | | | | | | |
| --- | --- | --- | --- | --- | --- | --- | --- | --- | --- | --- |
| | 1 | 2 | 3 | 4 | 5 | 6 | 7 | 8 | 9 | 10 |
| Sodium sulphite | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 |
| Ammonium Carbonate | 5 | 6.0 | 5.0 | — | 4.0 | 8.0 | 2.0 | — | 5.0 | 6.0 |
| Potassium Hydrogen Carbonate | — | — | 1.5 | 2.0 | — | — | 2.0 | 8.0 | — | — |
| Ammonium Acetate | — | — | — | 2.0 | — | — | — | 3.0 | — | — |
| Sodium Glycinate | — | 5.0 | — | 1.0 | — | — | — | — | — | — |
| Glutamine Acid | — | — | — | 2.0 | — | 6.0 | 2.0 | — | — | — |
| Glucosamine | — | — | — | — | — | — | 2.0 | — | 4.0 | — |
| Ceteareth-25 | 1.0 | — | — | — | — | — | — | 1.0 | 1.0 | 1.0 |
| Steareth-100 | — | 1.0 | 1.0 | — | — | — | — | — | — | — |
| Sodium Palmytoyl Sarcosinate | — | — | — | — | 1.0 | — | — | — | — | — |
| Sodium Carboxymethyl Lauryl Glucoside | — | — | — | 1.0 | — | — | — | — | — | — |
| Sodium Lauryl Sulfate | — | — | — | — | — | 1.0 | — | — | — | — |
| Behentrimonium Chloride | — | — | — | — | — | — | 1.0 | — | — | — |
| Cetyl Alcohol | 1.6 | — | 2 | 1.5 | 1.5 | 1.5 | 2.5 | 2.5 | 1.6 | 1.6 |
| Stearyl Alcohol | 3.3 | — | 2 | 1.5 | 1.5 | 1.5 | 2.5 | 2.5 | 3.3 | 3.3 |
| Steareth-2 | — | 5 | 1 | — | — | — | — | — | — | — |
| Sodium Benzoate | 0.1 | 0.1 | 0.1 | 0.1 | 0.1 | 0.1 | 0.1 | 0.1 | 0.1 | 0.1 |
| Phenoxyethanol | 0.1 | 0.1 | 0.1 | 0.1 | 0.1 | 0.1 | 0.1 | 0.1 | 0.1 | 0.1 |
| EDTA (tetrasodium salt) | 0.1 | 0.1 | 0.1 | 0.1 | 0.1 | 0.1 | 0.1 | 0.1 | 0.1 | 0.1 |
| p-phenylene diamine | — | — | 0.6 | 0.1 | 0.8 | — | — | 0.1 | 0.8 | — |
| p-amino phenol | — | 0.3 | — | 0.4 | — | 0.3 | — | 0.4 | — | 0.3 |
| 2,5-diaminotoluene sulphate | — | 0.1 | 0.2 | — | — | 0.1 | — | — | — | 0.1 |

-continued

| Ingredient | \multicolumn{10}{c}{Formulation} | | | | | | | | | |
|---|---|---|---|---|---|---|---|---|---|---|
|  | 1 | 2 | 3 | 4 | 5 | 6 | 7 | 8 | 9 | 10 |
| m-aminophenol | — | — | 0.1 | — | 0.2 | — | — | — | 0.2 | — |
| Resorcinol | — | 0.5 | — | 0.4 | — | 0.5 | — | 0.4 | — | 0.5 |
| napthol | — | — | 0.2 | — | 0.03 | — | — | — | 0.03 | — |
| 4-amino-2-hydroxy toluene | — | 0.2 | — | 0.3 | — | 0.2 | — | 0.3 | — | 0.2 |
| Basic Brown 17 | 0.3 | — | — | 0.1 | — | — | — | — | — | — |
| HC Blue 2 | — | — | — | — | — | — | — | 0.3 | — | — |
| Acid Violet 43 | — | — | — | — | — | — | — | 0.1 | — | 0.3 |
| Basic Orange 69 | — | — | — | — | — | — | — | — | 0.2 | — |
| HC Yellow 2 | — | 0.2 | — | — | — | 0.2 | — | — | — | — |
| Basic Yellow 57 | — | 0.2 | — | — | 0.1 | — | 0.1 | — | — | — |
| HC Red 3 | 0.1 | — | — | — | — | — | 0.2 | — | 0.1 | — |
| Basic Orange 31 | — | — | 0.3 | — | 0.2 | 0.3 | — | — | — | 0.1 |
| Basic yellow 87 | — | — | 0.1 | 0.3 | — | — | — | — | — | — |
| Hydrogen Peroxide (35% active) | 8.6 | 8.6 | 8.6 | 12.9 | 17 | 17 | 17 | 10.7 | 10.7 | 10.7 |
| Amodimethicone (Belsil ADM1100) | 1.5 | — | — | — | — | — | — | — | 1.0 | — |
| Trimethylsilylamo-dimethicone (SF1708) | — | 0.5 | — | — | — | — | — | 2.0 | — | — |
| Polyquaternium-22 (Merquat 295) | — | — | 2.0 | — | 0.1 | — | — | — | — | — |
| Polyquaternium-37 & Mineral oil (Salcare SC95) | — | — | — | 0.5 | 0.1 | — | — | — | — | — |
| Polyquaternium 10 (Polymer JR30M) | — | — | — | — | — | 0.2 | 0.2 | — | — | — |
| Dicetyldimonium Chloride | — | — | — | — | — | — | — | — | 0.2 | — |
| Xanthan gum | 0.1 | 0.5 | — | — | 0.2 | — | — | — | — | — |
| Cetyl hydroxyethyl Cellulose (Natrosol 330CS Plus) | — | — | 0.8 | — | — | — | — | — | — | — |
| pH adjust to pH 9.0 | qs | qs | qs | qs | qs | qs | qs | qs | qs | qs |
| Water | qs | qs | qs | qs | qs | qs | qs | qs | qs | qs |

Examples of Emulsion Formulations 11-20

| Ingredient | \multicolumn{10}{c}{Formulation} | | | | | | | | | |
|---|---|---|---|---|---|---|---|---|---|---|
|  | 11 | 12 | 13 | 14 | 15 | 16 | 17 | 18 | 19 | 20 |
| Sodium sulphite | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 |
| Ammonium Carbonate | 5.0 | 6.0 | 5.0 | — | 4.0 | 8.0 | 2.0 | — | 5.0 | 6.0 |
| Potassium Hydrogen Carbonate | — | — | 1.5 | 2.0 | — | — | 2.0 | 8.0 | — | — |
| Ammonium Acetate | — | — | — | 2.0 | — | — | — | 3.0 | — | — |
| Sodium Glycinate | — | 5.0 | — | 1.0 | — | — | — | — | — | — |
| Glutamine Acid | — | — | — | 2.0 | — | 6.0 | 2.0 | — | — | — |
| Glucosamine | — | — | — | — | — | — | 2.0 | — | 4.0 | — |
| Crodafos ® CES | 2.0 | 3.0 | 1.5 | 3.0 | 3.0 | 3.0 | 3.0 | 3.0 | 3.0 | 3.0 |
| EDTA (tetrasodium salt) | 0.1 | 0.1 | 0.1 | 0.1 | 0.1 | 0.1 | 0.1 | 0.1 | 0.1 | 0.1 |
| p-phenylene diamine | — | — | 0.6 | 0.1 | 0.8 | — | — | 0.1 | 0.8 | — |
| p-amino phenol | — | 0.3 | — | 0.4 | — | 0.3 | — | 0.4 | — | 0.3 |
| 2,5-diaminotoluene sulphate | — | 0.1 | 0.2 | — | — | 0.1 | — | — | — | 0.1 |
| m-aminophenol | — | — | 0.1 | — | 0.2 | — | — | — | 0.2 | — |
| Resorcinol | — | 0.5 | — | 0.4 | — | 0.5 | — | 0.4 | — | 0.5 |
| napthol | — | — | 0.2 | — | 0.03 | — | — | — | 0.03 | — |
| 4-amino-2-hydroxy toluene | — | 0.2 | — | 0.3 | — | 0.2 | — | 0.3 | — | 0.2 |
| Basic Brown 17 | 0.3 | — | — | 0.1 | — | — | — | — | — | — |
| HC Blue 2 | — | — | — | — | — | — | — | 0.3 | — | — |
| Acid Violet 43 | — | — | — | — | — | — | — | 0.1 | — | 0.3 |
| Basic Orange 69 | — | — | — | — | — | — | — | — | 0.2 | — |
| HC Yellow 2 | — | 0.2 | — | — | — | 0.2 | — | — | — | — |
| Basic Yellow 57 | — | 0.2 | — | — | 0.1 | — | 0.1 | — | — | — |
| HC Red 3 | 0.1 | — | — | — | — | — | 0.2 | — | 0.1 | — |
| Basic Orange 31 | — | — | 0.3 | — | 0.2 | 0.3 | — | — | — | 0.1 |
| Basic yellow 87 | — | — | 0.1 | 0.3 | — | — | — | — | — | — |
| Hydrogen Peroxide (35% active) | 8.6 | 8.6 | 8.6 | 12.9 | 17 | 17 | 17 | 10.7 | 10.7 | 10.7 |

-continued

| Ingredient | Formulation | | | | | | | | | |
|---|---|---|---|---|---|---|---|---|---|---|
| | 11 | 12 | 13 | 14 | 15 | 16 | 17 | 18 | 19 | 20 |
| Amodimethicone (Belsil ADM1100) | 1.5 | — | — | — | — | — | — | — | 1.0 | — |
| Trimethylsilylamo-dimethicone (SF1708) | — | — | — | — | — | — | — | 2.0 | — | — |
| Polyquaternium-22 (Merquat 295) | — | — | 2.0 | — | 0.5 | — | — | — | — | — |
| Polyquaternium-37 & Mineral oil (Salcare SC95) | — | — | — | 0.5 | 0.1 | — | — | — | — | — |
| Polyquaternium 10 (Polymer JR30M) | — | — | — | — | — | 0.2 | 0.2 | — | — | — |
| Dicetyldimonium Chloride | — | — | — | — | — | — | — | — | 0.2 | — |
| Xanthan gum | 0.1 | — | 0.2 | 0.2 | — | — | — | — | — | — |
| Succinoglycan | — | — | — | — | 0.2 | 0.5 | — | — | — | — |
| Carbomer | — | — | — | — | — | — | 1.0 | 0.5 | — | — |
| Acrylates/C10-30 Alkyl Acrylate Crosspolymer | — | — | — | — | — | — | — | 0.5 | — | — |
| Hydroxyethyl cellulose | — | — | — | — | — | — | — | — | 0.5 | — |
| Hydroxypropyl Starch Phosphate | — | — | — | — | — | — | — | — | — | 2.0 |
| pH adjust to pH 9.0 | qs | qs | qs | qs | qs | qs | qs | qs | qs | qs |
| Water | qs | qs | qs | qs | qs | qs | qs | qs | qs | qs |

Examples of Thickened Aqueous Solution Formulations 1-10

| Ingredient | Formulation | | | | | | | | | |
|---|---|---|---|---|---|---|---|---|---|---|
| | 1 | 2 | 3 | 4 | 5 | 6 | 7 | 8 | 9 | 10 |
| Sodium sulphite | 0.1 | 0.1 | 0.1 | 0.1 | 0.1 | 0.1 | 0.1 | 0.1 | 0.1 | 0.1 |
| Ascorbic Acid | 0.1 | 0.1 | 0.1 | 0.1 | 0.1 | 0.1 | 0.1 | 0.1 | 0.1 | 0.1 |
| Citric Acid | 1.0 | 1.0 | 1.0 | 1.0 | 1.0 | 1.0 | 1.0 | 1.0 | 1.0 | 1.0 |
| Ammonium Carbonate | 5.0 | 6.0 | 5.0 | — | 4.0 | 8.0 | 2.0 | — | 5.0 | 6.0 |
| Potassium Hydrogen Carbonate | — | — | 1.5 | 2.0 | — | — | 2.0 | 3.0 | — | — |
| Ammonium Acetate | — | — | — | 2.0 | — | — | — | 3.0 | — | — |
| Sodium Glycinate | — | 5.0 | — | 1.0 | — | — | — | — | — | — |
| Glutamic Acid | — | — | — | 2.0 | — | 6.0 | 2.0 | — | — | — |
| Glucosamine | — | — | — | — | — | — | 2.0 | — | 4.0 | — |
| Oleth 10 | 1.0 | 1.0 | 1.0 | 1.0 | — | — | — | — | — | — |
| Oleth 2 | 0.8 | 0.8 | 0.8 | 0.8 | — | — | — | — | — | — |
| Oleic Acid | 0.9 | 0.9 | 0.9 | 0.9 | — | — | — | — | — | — |
| Cocamide DEA | 3.0 | 3.0 | 3.0 | 3.0 | — | — | — | — | — | — |
| EDTA (tetrasodium salt) | 0.1 | 0.1 | 0.1 | 0.1 | 0.1 | 0.1 | 0.1 | 0.1 | 0.1 | 0.1 |
| p-phenylene diamine | — | — | 0.6 | 0.1 | 0.8 | — | — | 0.1 | 0.8 | — |
| p-amino phenol | — | 0.3 | — | 0.4 | — | 0.3 | — | 0.4 | — | 0.3 |
| 2,5-diaminotoluene sulphate | — | 0.1 | 0.2 | — | — | 0.1 | — | — | — | 0.1 |
| m-aminophenol | — | — | 0.1 | — | 0.2 | — | — | — | 0.2 | — |
| Resorcinol | — | 0.5 | — | 0.4 | — | 0.5 | — | 0.4 | — | 0.5 |
| napthol | — | — | 0.2 | — | 0.03 | — | — | — | 0.03 | — |
| 4-amino-2-hydroxy toluene | — | 0.2 | — | 0.3 | — | 0.2 | — | 0.3 | — | 0.2 |
| Basic Brown 17 | 0.3 | — | — | 0.1 | — | — | — | — | — | — |
| HC Blue 2 | — | — | — | — | — | — | — | 0.3 | — | — |
| Acid Violet 43 | — | — | — | — | — | — | — | 0.1 | — | 0.3 |
| Basic Orange 69 | — | — | — | — | — | — | — | — | 0.2 | — |
| HC Yellow 2 | — | 0.2 | — | — | — | 0.2 | — | — | — | — |
| Basic Yellow 57 | — | 0.2 | — | — | 0.1 | — | 0.1 | — | — | — |
| HC Red 3 | 0.1 | — | — | — | — | — | 0.2 | — | 0.1 | — |
| Basic Orange 31 | — | — | 0.3 | — | 0.2 | 0.3 | — | — | — | 0.1 |
| Basic yellow 87 | — | — | 0.1 | 0.3 | — | — | — | — | — | — |
| Hydrogen Peroxide (35% active) | 8.6 | 8.6 | 8.6 | 13 | 17 | 17 | 17 | 10.7 | 10.7 | 10.7 |
| Polyquaternium-22 (Merquat 295) | — | — | — | — | 0.5 | — | — | — | — | — |
| Polyquaternium-37 & Mineral oil (Salcare SC95) | — | — | — | — | 0.1 | — | 0.5 | — | — | — |
| Amodimethicone (Belsil ADM1100) | — | — | — | — | — | 1.0 | — | — | — | — |

-continued

| Ingredient | Formulation | | | | | | | | | |
|---|---|---|---|---|---|---|---|---|---|---|
| | 1 | 2 | 3 | 4 | 5 | 6 | 7 | 8 | 9 | 10 |
| Acrylates Copolymer (Aculyn ® 33A) | 2.4 | 2.4 | 2.4 | 2.4 | — | — | — | — | — | — |
| Acrylates Steareth-20 Methacrylate Copolymer (Aculyn ® 22) | 0.5 | 0.5 | — | 1.0 | — | — | — | — | — | — |
| Xanthan gum | — | — | — | — | — | 1.0 | — | — | — | — |
| Succinoglycan | — | — | — | — | 0.8 | — | — | — | — | — |
| Carbomer | — | — | — | — | — | — | 2.0 | — | — | — |
| Acrylates/C10-30 Alkyl Acrylate Crosspolymer | — | — | — | — | — | — | — | 2.0 | — | — |
| Hydroxyethyl cellulose | — | — | — | — | — | — | — | — | 2.0 | — |
| Hydroxypropyl Starch Phosphate | — | — | — | — | — | — | — | — | — | 2.0 |
| Propylene Glycol | 8.2 | 8.2 | 8.2 | 8.2 | 8.0 | 8.0 | 8.0 | 8.0 | 8.0 | 8.0 |
| Ethoxy Diglycol | 4.2 | 4.2 | 4.2 | 4.2 | — | — | — | — | — | — |
| pH adjust to pH 9.0 | qs | qs | qs | qs | qs | qs | qs | qs | qs | qs |
| Water | qs | qs | qs | qs | qs | qs | qs | qs | qs | qs |

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are the scope of this invention.

What is claimed is:

1. A hair colouring or bleaching composition comprising
   i) at least one source of peroxymonocarbonate ions
   ii) at least one source of alkalising agent
   iii) at least one preformed dye
   wherein said composition has a pH of from about 7.5 to about pH 9.5.

2. A hair colouring or bleaching composition according to claim 1, wherein said source of peroxymonocarbonate ions comprises at least one source of hydrogen peroxide and at least one source of carbonate, carbamate, hydrogen carbonate ions, or mixtures thereof.

3. A hair colouring or bleaching composition according to claim 1, wherein said at least one preformed dye is selected from the group consisting of Basic Red 51, Basic Orange 31, Basic Yellow 87, Basic Blue 99, Basic Brown 16, Basic Red 76, Basic Yellow 57, Basic Brown 17, Basic Red 118, Basic Orange 69, HC Red 3 HC Blue 2, HC Yellow 2, Disperse Blue 377, Acid Violet 43, Solvent Violet 13, 2-amino-6-chloro-4-nitrophenol, and mixtures thereof.

4. A hair colouring or bleaching composition according to claim 1, wherein said composition further comprises an oxidative dye precursor, selected from the group consisting of: 2-methyl-benzene-1,4-diamine; benzene-1,4-diamine; N,N-Bis(2-hydroxyethyl)-p-phenylenediamine; 4-amino-phenol; 4-methylamino-phenol; 4-amino-3-methyl-phenol; 1-Hydroxy-2,4-diaminobenzene; 2-amino-phenol; 2-amino-5-methyl-phenol; 2-amino-6-methyl-phenol; 1-methyl-1H-pyrazole-4,5-diamine; 1-Hydroxyethyl-4,5-diaminopyrazole sulphate; 2-(4,5-diamino-1H-pyrazol-1-yl) ethanol; benzene-1,3-diol; 4-chlorobenzene-1,3-diol; 2-methyl-benzene-1,3-diol; benzene-1,3-diamine; 3-amino-phenol; 5-amino-2-methyl-phenol; 1-Methyl-2-hydroxy-4-(2'-hydroxyethyl)aminobenzene; 4-methyl-2-phenyl-2,4-dihydro-3H-pyrazol-3-one; 2-aminopyridin-3-ol; 1-phenyl-3-methylpyrazol-5-one; 1-Phenyl-3-methyl-5-pyrazolone-2,4-dihydro-5,2phenyl-3H-pyrazole-3-one and mixtures thereof.

5. A hair colouring or bleaching composition according to claim 2, wherein said composition comprises
   a. from about 0.1% to about 10% by weight of hydrogen peroxide
   b. from about 0.1 to about 10% by weight of said alkalising agent
   c. from about 0.1 to about 15% by weight of said at least one source of carbonate, carbamate, hydrogen carbonate ions, or mixtures thereof
   d. from about 0.01% to about 10.0% by weight of said at least one preformed dye.

6. A hair colouring or bleaching kit comprising
   i) a first individually packaged component comprising at least one source of hydrogen peroxide
   ii) a second individually packaged component comprising
      a) at least one source of carbonate ions, carbamate ions, hydrocarbonate ions. or mixtures thereof,
      b) at least one alkalising agent and
      c) at least one preformed dye
   wherein said first individually packaged component and said second individually packaged component are mixed to form a composition comprising peroxymonocarbonate ions and having a pH of from about 7.5 to about pH 9.5.

7. A method of oxidative colouring or oxidative bleaching of hair comprising the steps of applying a composition comprising at least one source of peroxymonocarbonate ions, at least one alkalizing agent and at least one preformed dye wherein said composition has a pH of from about 7.5 to about 9.5 for at least about 50% of the time period wherein said composition is applied and retained on the hair.

8. A method of oxiclative colouring or oxidative bleaching of hair comprising the steps of applying a composition according to claim 1, leaving said composition on the hair for from about 2 to about 60 minutes and subsequently rinsing said composition from the hair.

9. A method of oxidative colouring or bleaching of hair according to claim 8, wherein said composition is retained on the hair for a time period of less than about 20 minutes.

10. A method of sequential oxidative hair colouring or hair bleaching comprising the steps of at least two sequential oxidative hair colour or hair bleaching treatments wherein the time period between each treatment is from about 1 day to about 60 days, and wherein each treatment comprises the steps of providing a composition according to claim 1, applying said composition to the hair and retaining said composition on the hair for a time period of less than about 20 minutes and subsequently rinsing said composition from the hair.

* * * * *